United States Patent [19]

Okutani

[11] Patent Number: 5,273,892
[45] Date of Patent: Dec. 28, 1993

[54] ACID HETEROPOLYSACCHARIDE, SULFATED POLYSACCHARIDE AND PROCESS FOR PRODUCING THE SAME

[75] Inventor: Koichi Okutani, Takamatsu, Japan

[73] Assignee: Teikoku Seiyaku Kabushiki Kaisha, Kagawa, Japan

[21] Appl. No.: 822,858

[22] Filed: Jan. 21, 1992

[30] Foreign Application Priority Data

Jan. 21, 1991 [JP] Japan .................... 3-021685

[51] Int. Cl.$^5$ .................... C07H 5/04; C07H 5/06; C07H 13/12; C12P 1/00
[52] U.S. Cl. .................... 435/104; 435/874; 435/41; 536/53; 536/54; 536/118; 536/122; 536/123; 536/124
[58] Field of Search .................... 536/123, 122, 18.7, 536/54, 53, 124, 118; 435/874, 41, 104

[56] References Cited

U.S. PATENT DOCUMENTS

| | | | |
|---|---|---|---|
| 3,686,164 | 8/1972 | Unger et al. | 536/118 |
| 3,933,788 | 1/1976 | Kang et al. | 536/123 |
| 4,146,705 | 3/1979 | Knutson | 536/123 |
| 4,211,774 | 7/1980 | Kang et al. | 536/123 |
| 4,291,156 | 9/1981 | Kang et al. | 536/123 |
| 4,304,906 | 12/1981 | Kang et al. | 536/114 |
| 4,326,053 | 4/1982 | Kang et al. | 536/123 |
| 4,377,636 | 3/1983 | Kang et al. | 435/101 |
| 4,454,316 | 6/1984 | Veeder et al. | 536/123 |
| 4,535,153 | 8/1985 | Kang et al. | 536/123 |

FOREIGN PATENT DOCUMENTS

| | | |
|---|---|---|
| 0012552 | 12/1979 | European Pat. Off. |
| 4106041 | 7/1990 | European Pat. Off. |
| 2042359 | 2/1971 | France |

OTHER PUBLICATIONS

H. Nakashima et al., Jpn. J. Cancer Res., 78, 1164–1168 (1987).
M. Ito et al., Eur. J. Clin. Microbiol. Infect. Dis., 8, 171–173 (1989).
Carbohydr. Res., 199 77–82 (1990).
Biochem. J., 126, 395–407 (1972).
Baumann et al., Int. J. Syst. Bact., 33, 857–863 (1983).
Gavini et al., Int. J. Syst. Bact., 39, 135–144 (1989)
Nippon Suisan Gakkaishi 1845–1849 (1989).
K. Okutani et al., 'Isolation from fucosamine–containing ...' Nippon Suisan Gakkaishi, vol. 57, No. 11, 1991, pp. 2151–2156.
W. A. Corpe, 'An acid polysaccharide produced by a primary ...' Developments in Industrial Microbiology, vol. 11, 1970, pp. 402–412.
Suda Tandavanitj et al., 'The structural investigation of a sulfated ...', Nippon Suisan Gakkaishi, vol. 55, No. 10, 1989, pp. 1845–1849.
B. E. Christensen et al., 'Partial chemical and physical ...' Applied and Environmental Microbiology, vol. 50, No. 4, 1985, pp. 837–845.

Primary Examiner—Johnnie R. Brown
Assistant Examiner—Everett White
Attorney, Agent, or Firm—Birch, Stewart, Kolasch & Birch

[57] ABSTRACT

An acid heteropolysaccharide P-318 which comprises galactose, galacturonic acid, N-acetylfucosamine and pyruvic acid in a ratio of about 2:3:1:1, a sulfated heteropolysaccharide P-318 having a 10% or less sulfur content which is prepared by sulfating said acid heteropolysaccharide and a process for preparing an acid heteropolysaccharide P-318 which comprises culturing Pseudomonas sp. 318 to produce the acid heteropolysaccharide P-318 and collecting the thus produced acid heteropolysaccharide P-318. The sulfated polysaccharide P-318 of the invention shows a strong antiviral activity in spite of a lower content of sulfate.

3 Claims, 1 Drawing Sheet

ACID HETEROPOLYSACCHARIDE, SULFATED POLYSACCHARIDE AND PROCESS FOR PRODUCING THE SAME

The present invention relates to a novel acid heteropolysaccharide P-318, a sulfated heteropolysaccharide P-318 derived therefrom and useful as a medicament, and a process for producing said heteropolysaccharide using a microorganism.

PRIOR ART

It has been known that a sulfated polysaccharide shows an antiviral activity against herpes virus in vitro. In recent years, it has been found that the sulfated polysaccharide also shows an inhibitory action against retrovirus [cf. H. Nakashima et al., *Jpn. J. Cancer Res.*, 78, 1164–1168 (1987)]. Thereafter, there are many reports as to the action of sulfated polysaccharides which are prepared by sulfating polysaccharides obtained from animals, plants, microorganisms, etc. on retroviruses including AIDS (acquired immunodeficiency syndrome) virus [cf., for example, M. Ito et al., *Eur. J. Clin. Microbiol. Intect. Dis.*, 8, 171–173 (1989)].

It is well known that some microorganisms produce a polysaccharide. For example, microorganisms belonging to genera of Alcaligenes, Azotobacter, Bacillus, Xanthomonas, Pullularia, Vibrio, etc. are known to produce a polysaccharide. Also it is known that bacteria belonging to genus of Pseudomonas produce some kinds of polysaccharides. That is, it has been reported that *P. marqinalis* produces an acid polysaccharide [*Carbohydr. Res.*, 199, 77–82 (1990)] and *P. aeruqinosa* produces lipopolysaccharide [*Biochem. J.*, 126, 395–407 (1972)]. However, conventional sulfated polysaccharides using these polysaccharides have not yet been put to practical use, and novel sulfated polysaccharides are still desired.

BRIEF DESCRIPTION OF THE INVENTION

Under the circumstances, the present inventor has intensively studied as to useful substances produced by marine microorganisms isolated from the sea, and has found that some kind of bacterium belonging to genus *Pseudomonas*, which is isolated from intestine of *Stichopus japonicus*, produces a polysaccharide which comprises as a main constituent glucuronic acid, galactose, N-acetylfucosamine and pyruvic acid, that the thus produced polysaccharide is a novel water-soluble acid polysaccharide which is different from any hitherto known polysaccharides produced by microorganisms, and that a sulfated polysaccharide prepared by sulfating said polysaccharide shows antiviral activity in spite of a lower sulfur content.

An object of the present invention is to provide an acid heteropolysaccharide P-318 which comprises galactose, galacturonic acid, N-acetylfucosamine and pyruvic acid in a ratio of about 2:3:1:1.

Another object of the present invention is to provide a sulfated heteropolysaccharide P-318 having a sulfur content of 10 % or less, which is prepared by sulfating the above acid heteropolysaccharid.

Still another object of the present invention is to provide a process for preparing an acid heteropolysaccharide P-318 which comprises culturing Pseudomonas sp. 318 to produce the acid heteropolysaccharide P-318 and collecting the thus produced acid heteropolysaccharide P-318.

These and other objects and advantages of the invention will be apparent to those skilled in the art from the following description.

DETAILED DESCRIPTION OF THE INVENTION

Figure 1:
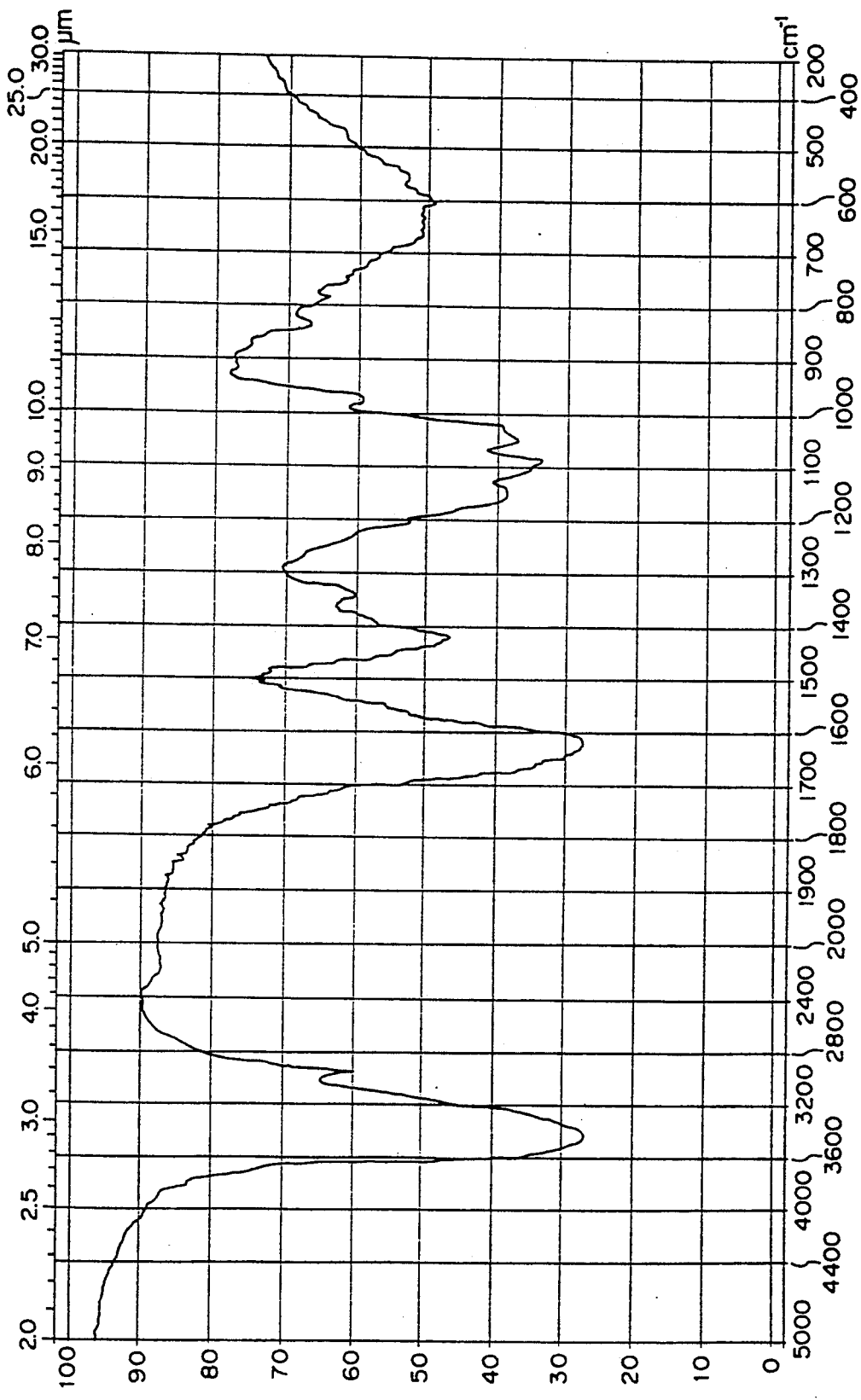
FIG. 1 is a graph showing the infrared spectrum of the polysaccharide P-318 of the invention.

As will be shown in detail by the analysis hereinbelow, the acid polysaccharide of the present invention (hereinafter also referred to as "P-318") comprises galactose, galacturonic acid, N-acetylfucosamine and pyruvic acid wherein the ratio of these components is 2:3:1:1. The sulfated polysaccharide of the present invention (hereinafter also referred to as "sulfated P-318") is prepared by esterification of the acid polysaccharide P-318 of the invention with sulfuric acid in usual manner. The sulfated P-318 of the present invention is characterized by a lower content of sulfuric acid than that of the conventional sulfated polysaccharides which are known to have an antiviral activity and are reported in terms of their content of sulfuric acid. Since a polysaccharide sulfate is known to have a strong toxicity against humans and animals, such a lower content of sulfuric acid makes the sulfated polysaccharide of the present invention quite advantageous for use as a medicament.

First of all, the present inventor has identified a novel bacterium belonging to the Pseudomonas genus which produces the acid polysaccharide of the present invention. As a result of taxological study in a vast range by the present inventor, the identified bacterium was found to be a novel microorganism which has hitherto not been described in the literature and the acid polysaccharide of the present invention could be prepared by culturing this bacterium in a suitable nutrient culture medium. The bacterium which the present inventor has isolated from the intestine of *Stichopus japonicus* had the following bacteriological properties wherein the bacterium was cultured in a basal medium supplemented with sea water or 3% NaCl.

1. Morphological observation:

| Shape: | Linear bacillus |
|---|---|
| Size: | 0.8 to 1.0 × 1.8 × 2.0 μm |
| Motility: | Yes |
| Sporulation: | No |
| Gram-stain: | Negative |

2. Cultural observation:
   Bouillon agar plate culture: medium growth, circular, semi-transparent, entire hem, convex, glossy, dim yellow.
   Bouillon liquid culture: medium growth

| Growth temperature: | 25° C. + |
|---|---|
| | 37° C. + |
| | 41° C. − |

3. Physiological properties:

| Catalase: | + |
|---|---|
| Oxidase (Kovac's) | + |
| O-F Test: | |

| -continued | |
|---|---|
| Oxidation | + |
| Fermentation | − |
| Reduction of nitrate: | + |
| Production of indole: | − |
| Arginine dihydrolyase: | − |
| Decarboxylation of lysine: | − |
| β-Galactosidase: | − |
| Utilization of D-glucose: | + |
| Utilization of L-arabinose: | − |
| Utilization of D-mannose: | − |
| Utilization of D-mannitol: | − |
| Utilization of N-acetylglucosamine: | − |
| Utilization of maltose: | − |
| Utilization of gluconate: | − |
| Utilization of caproate: | + |
| Utilization of adipate: | + |
| Utilization of malate: | + |
| Utilization of citrate: | − |
| Utilization of phenyl acetate: | − |
| Hydrolysis of gelatin: | − |
| Hydrolysis of casein: | − |
| Hydrolysis of starch: | − |
| Hydrolysis of Tween 80: | + |
| Hydrolysis of urea: | − |
| Hydrolysis of esculin: | − |
| Hydrolysis of DNA: | − |
| Production of levan from sucrose | − |
| Use of tartrate: | − |
| Use of malonate: | − |
| Use of hydrogen sulfide: | − |
| Use of citric acid: | − |
| Drug sensitivity: | |
| Penicillin | − |
| Streptomycin | + |
| Chloramphenicol | + |
| Tetracyclin | + |
| Novobiocin | − |
| Polymyxin B | + |

Based on the above bacteriological properties, this bacterium is recognized to belong to genus of Pseudomonas. A variety of taxological clues of Pseudomonas genus and culture of Pseudomonas bacteria are described in Bergey's Manual of Systematic Bacteriology [Krieg et al., 1980] Vol. 1; Taxology of marine Pseudomonas [Baumann et al., Int. J. Syst. Bact., 33, 587–863 (1983)]; Numerical taxonomy of Pseudomonas [Gavini et al., Int. J. Syst. Bact., 39, 135–144 (1989)]; and Method for study of marine microorganism [Kadota et al, 1985] and the like. Based on these clues and descriptions, there were searched for microorganisms belonging to Pseudomonas having the same morphological, cultural and biochemical characteristics as those of the bacterium of the present invention.

According to the search based on the clues and the above-mentioned literatures, the strain of the present invention is similar to *Pseudomonas alcaligenes* or *Comamonas testosteronii*. However, the strain of the present invention is different from these strains in that *Comamonas testosteronii* is devoid of utilization of glucose and *Pseudomonas alcaligenes* subgroup A2 (Gavini et al., 1989), which is the only strain of *P. alcaligenes* having glucose utilization, shows differences in the reduction of nitrate and utilization of caproic acid. Accordingly, the strain of the present invention was identified as a novel marine Pseudomonas strain which hitherto has not been named. The strain of the present invention has been deposited at Fermentation Research Institute, Agency of Industrial Science and Technology, as Pseudomonas sp. 318 BIKOKEN No. 11949; FERM P-11949 dated Jan. 11, 1991, which was changed to a deposit under Budapest Treaty on Jan. 16, 1992 as accession number of "FERM BP-3708".

The acid polysaccharide P-318 of the present invention can be produced in an aerobic culture by inoculating the above-mentioned Pseudomonas microorganism of the invention in a suitable nutrient culture medium and culturing it under regulatory conditions. The culture medium used for culturing the microorganism of the present invention may be a usual culture medium containing carbon, nitrogen, an inorganic salt, and the like. A carbon source for assimilation in the nutrient medium is generally a carbohydrate, e.g. glucose, sucrose, etc. and these carbon sources can be used alone or in a combination thereof. An accurate amount of the carbon source or carbon sources used in the culture medium is generally in a range of 1 to 3% (% by weight, all percentages disclosed hereinafter are the same) per total amount of the culture medium, although it may vary depending on the kind and amount of other components contained in the culture medium. Each of these carbon sources can be used alone, or several carbon sources can be used in combination in the culture medium.

As a nitrogen source in the culture medium, various proteincceous substances can generally be used. Suitable of the nitrogen source are a meat extract, peptone, a yeast extract, a hydrolysate of casein, soybean, and the like. Each of these nitrogen sources can be used alone, or several nitrogen sources can be used in combination in an amount ranging from 0.05 to 0.6 % per total amount of the culture medium.

A nutrient inorganic salt to be used in the culture medium includes any ion contained in sea water. Such ions include metal ions contained in sea water in trace amounts, such as cobalt ion, manganese ion, iron ion, magnesium ion, etc. as well as the usual salts releasing sodium ion, potassium ion, ammonium ion, calcium ion, phosphate ion, sulfate ion, chloride ion, carbonate ion, etc. Although a specific culture medium having a specific composition is shown in the Examples hereinbelow, such a culture medium is selected merely as one embodiment from various culture media applicable in the present invention.

The culture is conducted at a temperature ranging from about 25° to 32° C., preferably at a temperature ranging from about 26° to 28° C. for optimum results. The culture medium has a pH value of about 6 to 8 and the culture time is usually in a range of 3 to 4 days although it may vary depending on a variety of culture conditions. The acid polysaccharide of the present invention can be produced either on an agar plate or in a liquid culture medium, preferably in a liquid culture medium. The thus produced acid polysaccharide of the present invention can be collected by conventional known methods. For example, the polysaccharide of the present invention can be collected by removing microorganism cells from the culture liquid through isolation procedures such as centrifugation, filtration, etc., followed by addition of a precipitating agent such as methanol, ethanol, acetone, etc. Alternatively, considering that the polysaccharide of the present invention is an acid substance, it can also be collected by adding a quaternary ammonium salt such as cetyl trimethyl ammonium bromide to the culture liquid wherein the microorganism cells are removed.

The crude polysaccharide of the present invention can be purified by known methods for purification of polysaccharides. For example, a purified polysaccharide of high purity can be obtained as a white cotton by redissolving the crude polysaccharide of the present invention in water, adding a precipitating agent such as ethanol to the solution, subjecting to dialysis followed by lyophilization. The above purification procedure can also be used in combination with the precipitation procedure by a quaternary ammonium salt such as cetyl trimethyl ammonium bromide.

The present invention is described in more detail by the following Examples but should not be construed to be limited thereto.

EXAMPLE 1

A culture medium prepared from sea water having a composition of 3% sucrose, 0.5% peptone and 0.1% yeast extract was sterilized in an autoclave at 121° C. for 20 minutes. One platinum loop of Pseudomonas sp. 318 (FERM P-11949) from a slant culture for preservation was inoculated into the above sterilized culture medium (10 ml) in a test tube and the test tube was shaked at 28° C. for 48 hours. Then, this preculture solution was inoculated into the above sterilized culture medium (1 L) in a 5 liter Erlenmeyer flask and a shaking culture was conducted at 28° C. for 4 days. After culture, the culture solution was subjected to centrifugation to remove microorganism cells and then twice the amount of ethanol was added to the supernatant to give a white precipitate. The resultant precipitate was collected and dissolved in water (300 ml). To the solution was then gradually added 5% cetyl trimethyl ammonium bromide solution until additional precipitates were not formed. As a result, the polysaccharide of the present invention was precipitated as a complex with cetyl trimethyl ammonium bromide. This complex was washed with water to remove excess cetyl trimethyl ammonium bromide and then dissolved in an aqueous solution (300 ml) of 4M sodium chloride. To this solution was added twice the amount of ethanol to precipitate the polysaccharide of the present invention. This procedure of ethanol precipitation was further repeated twice. The obtained precipitate was dissolved in water, the solution was dialyzed against water, followed by freeze-drying to give a purified polysaccharide of the present invention (0.7 g).

Analysis of constituent sugars of the polysaccharide of the present invention, i.e. a neutral sugar and an aminosugar, was carried out by hydrolyzing the polysaccharide of the present invention with 2M trifluoroacetic acid at 100° C. for 12 hours, removing trifluoroacetic acid, and conducting a down-flow paper chromatography with Whatman No. 1 chromatography paper wherein a mixture of ethyl acetate : acetic acid : formic acid : water (18:3:1:4) was used as a developing solution. A chromatography paper was immersed in alkaline silver nitrate and dyed with ninhydrin and aniline hydrogen phthalic acid spray reagent. The constituent sugars were identified by conducting simultaneous chromatography with standard sugars. By this method, there were detected galactose, uronic acid and aminosugar.

Further, the polysaccharide of the present invention was hydrolyzed in the same manner and the acid was removed. Then, the neutral sugar and aminosugar were converted to alditol acetate derivatives and subjected to a temperature programming gas chromatography at 190° to 250° C. with Hitachi 263-30 Gas Chromatograph provided with Uniport HP (80 to 100 mesh; manufactured by Gasukuro Kogyo K.K., Japan) column retaining 3% OV-225. As a result, galactose and fucosamine were identified by a simultaneous chromatography with standard sugars and xylose was quantified as an inner standard substance. In addition to these procedures, fucosamine was also identified by amino acid automatic analysis of the acid hydrolysate.

Quantification of a uronic acid content in the polysaccharide was conducted by two different methods, i.e. colorimetry with carbazole wherein the content of uronic acid is measured in terms of galacturonic acid [Sogo Tato Kagaku, No. 1, Harada et al., 1973] and a method wherein the uronic acid was converted to a methyl ester with 3% methanol/hydrochloric acid, the carboxyl group of uronic acid was reduced with sodium borohydride, the reduced uronic acid was hydrolyzed and the produced neutral sugars were analyzed to identify and quantify the original uronic acid. According to these methods, the uronic acid in the polysaccharide of the present invention was identified as galacturonic acid.

Using electrophoresis with cellulose acetate membrane, there were experimentally identified uronic acid, neutral sugar and aminosugar. The hydrolysate in a fixed amount, and uronic acid, neutral sugar and aminosugar standards were placed on a cellulose acetate membrane (Zartrius 11200) and electrophoresis was conducted at 150 V for 25 minutes using an Atoh electrophoresis device in 0.05M borate buffer (pH 7). A chromatogram was immersed in alkaline silver nitrate. Neutral sugar, galacturonic acid and fucosamine were estimated from colored spots.

Identification and quantification of pyruvic acid were made by proton nuclear magnetic resonance ($^1$H NMR) analysis and ion chromatography analysis. $^1$H NMR was carried out using heavy water as a solvent, sodium 2,2-di-methyl-2-silanopentane-5-sulfonate (DSS) as an inner standard and GSX-500 (500 MHz) nuclear magnetic resonance device manufactured by Nippon Denshi K.K., Japan. The proton due to methyl group usually appears at a range of 1.0 to 2.5 ppm. The proton at 1.24 ppm is derived from a methylated sugar, in this case, fucosamine. The proton at 1.45 ppm is derived from pyruvic acid and the proton at 2.04 ppm is derived from N-acetyl group. These data show the presence of both fucosamine and pyruvic acid, and that the fucosamine is N-acetylated. On the other hand, the polysaccharide of the present invention was hydrolyzed with 0.05M trifluoroacetic acid at 100° C. for 2 hours, and after neutralization, a content of pyruvic acid was measured using Shimazu Ion Chromatograph HIC-6A provided with Sympack 101H column (8.0 ×300 mm) and 0.5 mM perchloric acid as a mobile phase.

From the above results, it was found that the polysaccharide of the present invention is an acid heteropolysaccharide which comprises galactose, galacturonic acid, N-acetylfucosamine and pyruvic acid as main components wherein the ratio of galactose:galacturonic acid:N-acetylfucosamine:pyruvic acid is about 2:3:1:1.

The polysaccharide of the present invention has the following physicochemical properties:

Physicochemical Properties of the Polysaccharide P-318

1. Appearance:
White powder, no taste, no smell
2. Uniformity:
Having high uniformity since a single band is shown in centrifugation and a single band dyed with arsine blue is shown in electrophoresis with a cellulose acetate membrane.

3. Molecular weight:

$1.5 \times 10^8$ [gel filtration using Hitachi 655 high performance liquid chromatography provided with Asahipack GFA-7M column (Asahi Kasei K.K., $8.0 \times 500$ mm), standard: Shordex Standard P-82 (Showa Denko K.K.)]

4. Melting point:

Melting point is not clearly shown but it decomposes at around 260° C. and is browned.

5. Solubility:

Soluble in water, formamide and DMSO, but insoluble in methanol, ethanol, acetone, propanol, n-butanol, ethyl acetate, hexane, benzene, ether and chloroform.

6. Color reaction:

| Anthrone reaction: | positive |
| --- | --- |
| Molisch's reaction: | positive |
| Cysteine sulfate reaction: | positive |
| Phenol sulfate reaction: | positive |
| Carbazole reaction: | positive |
| Ninhydrin reaction: | positive |

(After hydrolysis with 2 N trifluoroacetic acid at 100° C. for 12 hours)

7. Specific rotation: $[\alpha]^{25}_{589} = +109°$ in 0.5 % aqueous solution

8. Infrared spectrum:

Infrared absorption spectrum by KBr tablet method is shown in FIG. 1.

9. Ultraviolet absorption spectrum:

No specific absorption is observed.

EXAMPLE 2

Chlorosulfonic acid was added dropwise to a solution of polysaccharide P-318 in formamide maintained at 0° C. while stirring and the reaction was conducted for 60 minutes and thereto was then added barium carbonate for neutralization. The resulting solution was dialyzed, twice the amount of ethanol was added and the formed precipitate was collected and dissolved in water. The solution was dialyzed and freeze-dried to give a sulfated polysaccharide.

The obtained sulfated polysaccharide has the following physicochemical properties. Sulfated polysaccharide P-318

The sulfated polysaccharide P-318 comprises galactose, galacturonic acid, N-acetylfucosamine, pyruvic acid and sulfate group, wherein the molar ratio of galactose galacturonic acid:N-acetylfucosamine:pyruvic acid is the same as that of polysaccharide P-318, and is formed by binding sulfate group (about 3.5 to 6.5% for S) to polysaccharide P-318. In this context, the S content means those derived from sulfate group or sulfonate group. The sulfated polysaccharide P-318 of the present invention has excellent characteristics for use as a medicament, in that it has a stronger antiviral activity than any known sulfated polysaccharide having an antiviral activity which occurs in nature or is synthesized by chemical modification, in spite of its lower content of sulfate. This is apparent from the results in the following Experiments.

Experiment 1

Action against herpes simplex virus type 1 KOS strain (HSV-1/KOS):

Vero cell was used as a host cell. Virus has been grown and stored with freezing ($-80°$C.) and the host cell has been cultured with passage. Eagle elementary medium (MEM: Nippon Seiyaku K.K.) containing 1.5% fetal bovine serum (FBS) was used as a culture medium for growth of HSV-1 and MEM containing 7.5% FBS was used as a culture medium for growth of the host cell.

(1) Cytopathic inhibitory effect (CPIE) test

For testing an antiviral activity of the sulfated polysaccharide P-318, cytopathic inhibitory effect (CPIE) test was conducted. That is, each 0.1 ml of a cell suspension (adjusted to $5 \times 10^5$/ml) was inoculated to each well of a 96-well plate and the cells were cultured under 5% $CO_2$ at 37° C. for about 24 hours to form a monolayer. Then, the culture solution was removed and the test dru9 (0.1 ml) was two-step diluted on the plate with the culture medium for 9growth of virus. For each diluted solution, 3 to 4 wells were employed. A virus solution (HSV-$1.3 \times 10^5$TCID$_{50}$/ml; 10 $\mu$l well) was inoculated and the cells were further cultured for 72 hours. Then, the culture solution was removed and the cells were fixed and dyed with 0.05% Crystal Violet - formalin for 20 to 30 minutes, washed with water and dried, and an absorbance (OD$_{590}$) was measured. Using the obtained absorbance (mean of absorbances from 3 to 4 wells), cytopathic inhibitory rate (viral growth inhibitory rate) in each concentration of the drug was calculated according to the following formula (1) and plotted on a one-sided logarithmic graph to obtain 50% cytopathic inhibitory concentration (CPIE$_{50}$).

$$\text{Cytopathic inhibitory rate} \\ (\%) = (ODs - ODi)/(ODc - ODi) \times 100 \quad (1)$$

ODc = OD$_{590}$ of cells not infected with virus
ODi = OD$_{590}$ of cells infected with virus
ODs = OD$_{590}$ of cells treated with drug and infected with virus (2) Cell Lethal Effect (CLE) Test For testing toxicity in host cells, cell lethal effect (CLE) test was conducted. The procedure in the above cytopathic inhibitory effect test was repeated except that the virus was not inoculated. According to the following formula (2), cell lethal rate was calculated in each concentration of the drug and plotted on a one-sided logarithmic graph to obtain 50% cell lethal concentration (CLE$_{50}$).

$$\text{Cell lethal rate } (\%) = (ODc - ODs)/ODc \times 100 \quad (2)$$

ODc = OD$_{590}$ of cells not treated with drug
ODs = OD$_{590}$ of cells treated with drug As a result of the above tests, it was found that the sulfated polysaccharide P-318 of the present invention had a strong activity against HSV-1 showing CPIE$_{50}$ of 0.21 $\mu$g/ml. It was also found that the sulfated polysaccharide P-318 of the invention had CLE$_{50}$ > 1000 $\mu$g/ml, and hence, did not show cytotoxicity against Vero cell up to a concentration of 1000 $\mu$g/ml. Sulfated P-318 of the invention showed a selective toxicity index of > 5000.

Experiment 2

The anti-AIDS virus activity of the sulfated polysaccharide P-318 of the present invention was tested by the following two methods.

Inhibitory Activity Against Protease of AIDS Virus

Using a synthesized peptide (Ser-Gln-Asn-Tyr-Pro-Ile-Val) as a substrate, cleavage of said substrate by HIV-1 protease prepared by genetic engineering techniques was monitored by a high performance liquid chromatography in order to measure inhibitory activity of the sulfated polysaccharide P-318.

In this test, the sulfated polysaccharide P-318 showed 50% inhibitory activity against HIV-1 protease at a concentration of 24 μg/ml. This value is smaller than that of pepstatin A which is known to inhibit HIV-1 protease.

Inhibitory Activity Against AIDS Viral Growth

Human lymphocytes (PBL-cell) were purified, concentrated and stimulated with a culture medium comprising RPMI 1640, 20% fetal calf serum, phytohemagglutinin (90 μg/ml) and interleukin 2 (40 μ/ml). PBL-cells were collected and reacted with AIDS virus HIV-1 at 37° C. for 1 hour, to let PBL-cells absorb the virus. The obtained virus-adsorbed cells were collected, washed with the culture medium and inoculated onto a 24-well plate at $1 \times 10^6$ cells. To each well was added a culture solution containing the sulfated polysaccharide P-318, and the cells were cultured at 37° C. for 3 to 5 days. Then, an antibody against the viral antigen was reacted with the cells and the rate of appearance of infected cells was measured by indirect fluorescent antibody method. As a result, the sulfated polysaccharide P-318 of the present invention showed 50% inhibitory activity against AIDS viral infection at a concentration of 10 μg/ml. In addition, the sulfated polysaccharide P-318 of the invention did not show cytotoxicity against PBL-cells at that concentration.

What is claimed is:

1. An acid heteropolysaccharide P-318 which comprises galactose, galacturonic acid, N-acetylfucosamine and pyruvic acid in a ratio of about 2:3:1:1.

2. A sulfated heteropolysaccharide P-318 having a 10% or less sulfur content which is prepared by sulfating the acid heteropolysaccharide P-318 which comprises galactose, galacturonic acid, N-acetylfucosamine and pyruvic acid in a ratio of about 2:3:1:1.

3. A process for preparing an acid heteropolysaccharide P-318 which comprises culturing Pseudomonas sp. 318 to produce the acid heteropolysaccharide P-318 and collecting the thus produced acid heteropolysaccharide P-318.

* * * * *